US011965837B2

(12) United States Patent
Beaupre et al.

(10) Patent No.: US 11,965,837 B2
(45) Date of Patent: Apr. 23, 2024

(54) SYSTEM AND METHODS FOR DETERMINING AIR CONTENT OF FRESH CONCRETE, AND CONCRETE MIXER TRUCK INCORPORATING SAME

(71) Applicant: COMMAND ALKON INCORPORATED, Birmingham, AL (US)

(72) Inventors: Denis Beaupre, Quebec (CA); Pierre Siccardi, Quebec (CA)

(73) Assignee: Command Alkon Incorporated, Birmingham, AL (US)

( * ) Notice: Subject to any disclaimer, the term of this patent is extended or adjusted under 35 U.S.C. 154(b) by 399 days.

(21) Appl. No.: 17/600,964

(22) PCT Filed: Mar. 31, 2020

(86) PCT No.: PCT/US2020/025890
§ 371 (c)(1),
(2) Date: Oct. 1, 2021

(87) PCT Pub. No.: WO2020/210080
PCT Pub. Date: Oct. 15, 2020

(65) Prior Publication Data
US 2022/0146440 A1     May 12, 2022

Related U.S. Application Data

(60) Provisional application No. 62/833,164, filed on Apr. 12, 2019.

(51) Int. Cl.
*G01N 23/083*     (2018.01)
*B28C 5/42*     (2006.01)
(Continued)

(52) U.S. Cl.
CPC .......... *G01N 23/083* (2013.01); *B28C 5/422* (2013.01); *G01N 23/10* (2013.01); *G01N 33/383* (2013.01);
(Continued)

(58) Field of Classification Search
CPC .... G01N 23/083; G01N 23/10; G01N 33/383; G01N 2223/04; G01N 2223/33;
(Continued)

(56) References Cited

U.S. PATENT DOCUMENTS 3,626,183 A    12/1971   Berry et al.
5,258,622 A *   11/1993   Pratt, Jr. .............. G01N 33/383
                                                          250/390.05
(Continued)

FOREIGN PATENT DOCUMENTS

JP    2002 307423 A    10/2002
JP    2012068194 A    4/2012
(Continued)

OTHER PUBLICATIONS

International Search Report and Written Opinion for PCT/US2020/025890 dated Jul. 9, 2020.

*Primary Examiner* — David P Porta
*Assistant Examiner* — Gisselle M Gutierrez
(74) *Attorney, Agent, or Firm* — Wiley Rein LLP (57) ABSTRACT

There is described a system for determining air content of fresh concrete received in a drum of a concrete mixer. The system generally has a high energy photon source mounted to the drum and emitting high energy photons towards a photon path rotating about a rotation axis as the drum rotates, the photon path is immersed in the fresh concrete during rotation, a photon detector mounted to the drum, the photon detector counting high energy photons received from the photon path; and generating a signal indicative of a (Continued)

number of counted events; a computing device determining an air content value of the fresh concrete based on the generated signal and on reference data; comparing the determined air content value to an air content threshold; and generating an alert based on the comparison to be displayed.

31 Claims, 8 Drawing Sheets

(51) Int. Cl.
    *G01N 23/10* (2018.01)
    *G01N 33/38* (2006.01)
    *G01P 15/00* (2006.01)
    *G08B 21/18* (2006.01)

(52) U.S. Cl.
    CPC ............ *G01P 15/00* (2013.01); *G08B 21/182* (2013.01); *G01N 2223/04* (2013.01); *G01N 2223/33* (2013.01); *G01N 2223/639* (2013.01)

(58) Field of Classification Search
    CPC ............ G01N 2223/639; G01N 23/223; B28C 5/422; B28C 7/024; G01P 15/00; G08B 21/182
    See application file for complete search history.

(56) References Cited

U.S. PATENT DOCUMENTS

| | | | |
|---|---|---|---|
| 7,569,810 B1 | 8/2009 | Troxler et al. | |
| 10,156,547 B2* | 12/2018 | Biesak | G01N 29/2468 |
| 11,312,039 B1* | 4/2022 | Chapdelaine | B28C 5/422 |
| 2014/0297204 A1* | 10/2014 | Biesak | G01N 29/2468 |
| | | | 702/56 |
| 2014/0373755 A1 | 12/2014 | Forgeron et al. | |
| 2022/0178806 A1* | 6/2022 | Biesak | G01N 33/383 |
| 2022/0355509 A1* | 11/2022 | Chapdelaine | B28C 7/024 |

FOREIGN PATENT DOCUMENTS

| | | |
|---|---|---|
| JP | 5 788157 A | 9/2015 |
| WO | 2018/0007396 A1 | 1/2018 |
| WO | 2018007396 A1 | 1/2018 |
| WO | 2019/040562 A1 | 2/2019 |
| WO | 2019040562 A1 | 2/2019 |

* cited by examiner

SYSTEM AND METHODS FOR DETERMINING AIR CONTENT OF FRESH CONCRETE, AND CONCRETE MIXER TRUCK INCORPORATING SAME

CROSS-REFERENCE TO RELATED APPLICATIONS

This application claims the benefit of U.S. provisional application No. 62/833,164, filed 12 Apr. 2019, which is hereby incorporated by reference as though fully set forth herein.

FIELD

The improvements generally relate to the handling of fresh concrete and more particularly relates to air content determination.

BACKGROUND

Fresh concrete is formed of a mixture of ingredients including at least cement-based material and water in given proportions. The ingredients are typically transported inside a drum of a mixer truck where the fresh concrete can be mixed prior to pouring.

In at least some situations, fresh concrete can be air-entrained meaning that the fresh concrete contains a significant number (e.g., billions) of microscopic air voids per cubic foot. It is known that these air voids can relieve internal pressure inside the fresh concrete by providing tiny chambers in which water can expand in freezing temperatures. Accordingly, air-entrained fresh concrete has been found to be particularly relevant in the context of northern climates where freezing and thawing cycle effects are not insignificant.

As air-entrained fresh concrete can be produced using air-entraining Portland cement in some cases, air-entraining agents can, alternately or additionally be incorporated into the fresh concrete in some other cases. Although producing air-entrained fresh concrete may appear somewhat straightforward, it must be produced under careful engineering supervision as the concrete is mixed to avoid undesirable situations where the fresh concrete would contain too few or too many air voids.

U.S. Pat. No. 10,156,547 B2 describes an acoustic-based air probe with an acoustic source configured to provide an acoustic signal into a mixture of fresh concrete, and an acoustic receiver configured to be substantially co-planar with the acoustic source and to provide signalling containing information such as air content about the mixture of fresh concrete. Although existing methods were satisfactory to a certain degree, there remains room for improvement, especially in terms of increasing the resolution, and/or accuracy of the air content measurements.

SUMMARY

As too few or too many air voids contained in a fresh concrete sample can inconveniently affect its durability against freezing and thawing cycle effects, monitoring air content over time from the moment where the ingredients are mixed to one another in a drum of a mixer truck to the moment where the air-entrained fresh concrete is delivered on site, with satisfactory resolution and/or accuracy, can be of importance.

The inventor found that to measure air content in fresh concrete being rotated in a drum of a mixer truck with an enhanced resolution and/or accuracy, unconventional measurements would have to be considered.

In an aspect of the present disclosure, there is described a concrete mixer truck having a frame, and a drum which is rotatably mounted to the frame and which receives air-entrained fresh concrete. The concrete mixer truck has a high energy photon source which is mounted to the drum. During use, the high energy photon source is configured to emit high energy photons towards a photon path rotating about the rotation axis as the drum rotates. It is intended that the photon path is immersed in the fresh concrete for at least a given period of time during rotation of the drum. In some embodiments, the high energy photon source emits high-energy X-ray photons whereas, in some other embodiments, the high energy photon source emits high energy gamma rays. The type of high energy photons thereby depends on the application and construction of the concrete mixer truck or measurement system. The photon path leads to a photon detector which is also mounted to the drum. The photon path can be configured in an attenuation configuration and/or in a Compton scattering configuration, depending on the embodiment. During use, the photon detector can count high energy photons received from the photon path at least during the above-mentioned period of time, and can generate a signal indicative of a number of counted events. Accordingly, using a computing device which is either mounted to the concrete mixer truck or remotely disposed, an air content value of the fresh concrete can be determined based on the generated signal and on reference data associating reference numbers of counted events to corresponding reference air content values. Accordingly, as the air-entrained fresh concrete is being mixed in the mixer truck, the computing device can compare the determined air content value against a given threshold, and generate an alert when the air content value of the fresh concrete is below and/or above a given air content threshold. In this aspect, the alert can be displayed at a user interface of the concrete mixer truck, thereby allowing an operator to modify the fresh concrete accordingly, prior to the pouring of the fresh concrete.

In accordance with a first aspect of the present disclosure, there is provided a system for determining air content of fresh concrete received in a drum of a concrete mixer, the system comprising: a high-energy photon source mounted to the drum, the high energy photon source emitting high energy photons towards a photon path rotating about a rotation axis as the drum rotates, the photon path being immersed in said fresh concrete for a given period of time during said rotating; a photon detector mounted to the drum and to which the photon path leads, the photon detector counting high energy photons received from the photon path at least during said period of time; and generating a signal indicative of a number of counted events; a computing device communicatively coupled with the photon detector, the computing device determining an air content value of the fresh concrete based on the generated signal and on reference data associating reference numbers of counted events to corresponding reference air content values; comparing said determined air content value to an air content threshold; and generating an alert based on said comparison; and a user interface communicatively coupled to the computing device and displaying said alert.

Further in accordance with the first aspect of the present disclosure, the high energy photon source can for example be an X-ray photon source or a gamma photon source.

Still further in accordance with the first aspect of the present disclosure, the photon path can for example extend linearly between the high energy photon source and the photon detector.

Still further in accordance with the first aspect of the present disclosure, the received photons can for example carry a photon energy similar to a photon energy of the emitted high energy photons, the generated signal being indicative of an attenuation between the emitted high energy photons and the received photons.

Still further in accordance with the first aspect of the present disclosure, the photon path can for example have a first path portion extending between the high energy photon source and a region immersed in said fresh concrete, and a second path portion extending between the region and the photon detector.

Still further in accordance with the first aspect of the present disclosure, the received photons can for example carry a photon energy different to a photon energy of the emitted high energy photons, the generated signal being indicative of Compton scattering occurring along the photon path.

Still further in accordance with the first aspect of the present disclosure, the system can for example further comprise at least an accelerometer for generating position data indicative of the position of the photon path relatively to the concrete mixer.

Still further in accordance with the first aspect of the present disclosure, both the high energy photon source and the photon detector can for example be mounted on an interior wall of the drum of the concrete mixer.

Still further in accordance with the first aspect of the present disclosure, the photon detector can for example be a first photon detector proximate to the high-energy photon source, in which case the system can for example comprise a second photon detector distal to the high-energy photon source.

In accordance with a second aspect of the present disclosure, there is provided a computer-implemented method for determining air content of fresh concrete received in a drum of a concrete mixer, the method comprising: receiving a signal indicative of a number of events counted by a photon detector following a high-energy photon source emitting high energy photons along a photon path leading to the photon detector during rotation of the drum; determining the number of events counted during a given period of time while the photon path is immersed in the fresh concrete received in the drum; matching the determined number of events to an air content value of the fresh concrete based on reference data associating reference numbers of counted events to corresponding reference air content values; comparing said air content value to an air content threshold; generating an alert based on said comparison; and displaying said alert.

Further in accordance with the second aspect of the present disclosure, the reference data can for example include a lookup table reference numbers of counted events to the corresponding reference air content values.

Still further in accordance with the second aspect of the present disclosure, said matching can for example include: looking up the reference data to find a given reference number of counted events corresponding to the number of counted events; and determining that the air content value corresponds to a reference air content value associated to the reference number of counted events.

Still further in accordance with the second aspect of the present disclosure, said looking up can for example include finding at least two reference numbers of counted events surrounding the number of counted events and extrapolating the air content value based on at least two reference air content values associated to the at least two reference numbers of counted events.

Still further in accordance with the second aspect of the present disclosure, the reference data can for example include a mathematical relation associating reference numbers of counted events to the corresponding reference air content values.

Still further in accordance with the second aspect of the present disclosure, said matching can for example include: inputting the number of counted events into the mathematical relation; and determining that the air content value corresponds to a result of said inputting.

Still further in accordance with the second aspect of the present disclosure, said reference data can for example be associated to a composition of said fresh concrete sample.

Still further in accordance with the second aspect of the present disclosure, the method can for example further comprise: prior to said matching, selecting the reference data associated to a composition of the fresh concrete sample among a plurality of reference data pertaining to a plurality of fresh concrete samples of different compositions; wherein said matching uses the selected reference data.

Still further in accordance with the second aspect of the present disclosure, the composition can for example be obtained from an input.

In accordance with a third aspect of the present disclosure, there is provided a computer-implemented method for producing reference data, the computer-implemented method comprising: receiving a reference number of counted events counted by a photon detector following a high-energy photon source emitting high energy photons along a photon path leading to the photon detector as the photon path is immersed in a fresh concrete sample for a given period of time; receiving a reference air content value indicative of an air content of the fresh concrete sample; repeating said receiving steps for a plurality of fresh concrete samples of the same composition and of different air contents; and producing reference data for the composition of fresh concrete by associating the reference numbers of counted events to the corresponding reference air content values.

Further in accordance with the third aspect of the present disclosure, the computer-implemented method can for example further comprise performing said receiving, repeating and producing steps for at least another composition of fresh concrete.

In accordance with a fourth aspect of the present disclosure, there is provided a concrete mixer truck comprising: a frame; a drum rotatably mounted to the frame, the drum receiving fresh concrete and having a rotation axis at least partially horizontally oriented relative to the vertical; a high energy photon source mounted to the drum, the high energy photon source emitting high energy photons towards a photon path rotating about the rotation axis as the drum rotates, the photon path being immersed in said fresh concrete for a given period of time during rotation of the drum; a photon detector mounted to the drum and to which the photon path leads, the photon detector counting high energy photons received from the photon path at least during said period of time; and generating a signal indicative of a number of counted events; a computing device communicatively coupled with the photon detector, the computing device determining an air content value of the fresh concrete based on the generated signal and on reference data associating reference numbers of counted events to corresponding reference air content values; comparing said determined air content value to an air content threshold; and generating an alert based on said comparison; and a user interface communicatively coupled to the computing device and displaying said alert.

Further in accordance with the fourth aspect of the present disclosure, the high energy photon source can for example be an X-ray photon source or a gamma photon source.

Still further in accordance with the fourth aspect of the present disclosure, wherein the photon path can for example extend linearly between the high energy photon source and the photon detector.

Still further in accordance with the fourth aspect of the present disclosure, the received photons can for example carry a photon energy similar to a photon energy of the emitted high energy photons, the generated signal being indicative of an attenuation between the emitted high energy photons and the received photons.

Still further in accordance with the fourth aspect of the present disclosure, the photon path can for example have a first path portion extending between the high energy photon source and a region immersed in said fresh concrete, and a second path portion extending between the region and the photon detector.

Still further in accordance with the fourth aspect of the present disclosure, the received photons can for example carry a photon energy different to a photon energy of the emitted high energy photons, the generated signal being indicative of Compton scattering occurring along the photon path.

Still further in accordance with the fourth aspect of the present disclosure, the concrete mixer truck can for example further comprise at least an accelerometer for generating position data indicative of the position of the photon path relatively to the concrete mixer.

Still further in accordance with the fourth aspect of the present disclosure, both the high energy photon source and the photon detector can for example be mounted on an interior wall of the drum of the concrete mixer.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
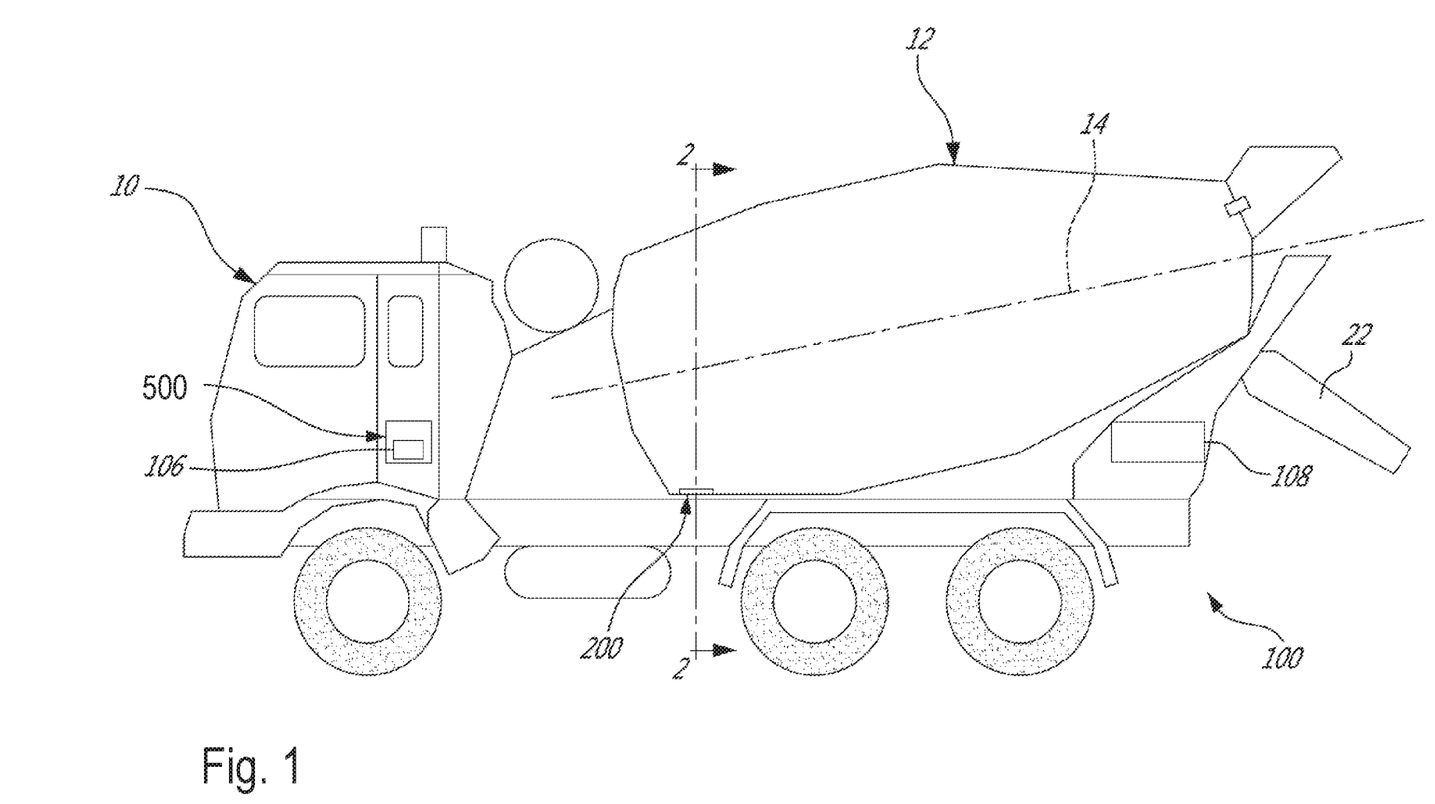
FIG. 1 is schematic view of an example of a concrete mixer truck incorporating a system for determining air content of the fresh concrete received in a drum of the concrete mixer truck, in accordance with one or more embodiments.

FIG. 1 shows an example of a concrete mixer used for handling fresh concrete. As depicted, the concrete mixer is provided in the form of a mixer truck 10 having a drum 12 rotatable about a rotation axis 14. During use, the drum 12 of the mixer truck 10 is loaded with fresh concrete. The fresh concrete includes a cement-based material and water. Air-entrained agents can also be incorporated into the fresh concrete to increase its air content. A composition of the fresh concrete is given by the relative amount of cement-base material, water and other components. The fresh concrete is then mixed inside the drum 12 by rotating it about the rotation axis 14 until it is poured at a desired location via a discharge chute 22 for the poured fresh concrete to harden into a desired structure of a given compressive strength. The air content of the fresh concrete can be used as an indication of the compressive strength once the fresh concrete has hardened in some embodiments.

A system 100 is provided for determining the air content value of the fresh concrete while it is being handled (e.g., mixed or poured) by the mixer truck 10. In the illustrated example, the system 100 includes a high-energy photon probing assembly 200 mounted inside the drum 12, and a computing device 500 communicatively coupled with the high energy probe assembly 200 using a wired connection, a wireless connection (e.g. Wifi™) or a combination thereof. A user interface 106 is typically mounted to the mixer truck 10. As will be described below, the user interface 106 is in wired and/or wireless communication with the computing device 500.

As shown, the high energy photon probing assembly 200 is mounted to the drum 12. In the illustrated embodiment, the high energy photon probing assembly 200 is mounted to an interior wall of the drum 12. However, in some other embodiments, the high energy photon probing assembly 200 can be mounted elsewhere relative to the drum 12. For instance, the high energy photon probing assembly 200 can be mounted proximate to the discharge chute 22. It is intended that some parts of the high energy photon probing assembly 200 can be mounted inside the drum 12 whereas some other parts of the high energy photon probing assembly 200 can be mounted outside the drum 12, depending on the embodiment.

In the illustrated embodiment, the computing device 500 is provided in the form of an on-board computer mounted a cabin of the mixer truck 10. The computing device 500 also incorporates the user interface 106. In an alternate embodiment, the computing device 500 can be provided in the form of a remote computer such as a hand-held device. The computing device 500 can communicate in a wired or in a wireless manner. In this example, the high energy photon probing assembly 200 communicates with the computing device 500 via a communicating unit 108. The communicating unit 108 is mounted to the mixer truck 10 and can act as a receiver for receiving electromagnetic signal(s) generated by the high energy photon probing assembly 200 and as a transmitter for transmitting the electromagnetic signal(s) to the computing device 500. The communicating unit 108 can allow communication between the computing device 500 and the high energy photon probing assembly 200 in a bidirectional manner in this example. The user interface 106 can be provided in the form of a display, a touch-sensitive display, LED lights, and/or any combination thereof. Any other suitable type of user interface can also be used.

Figure 2A:
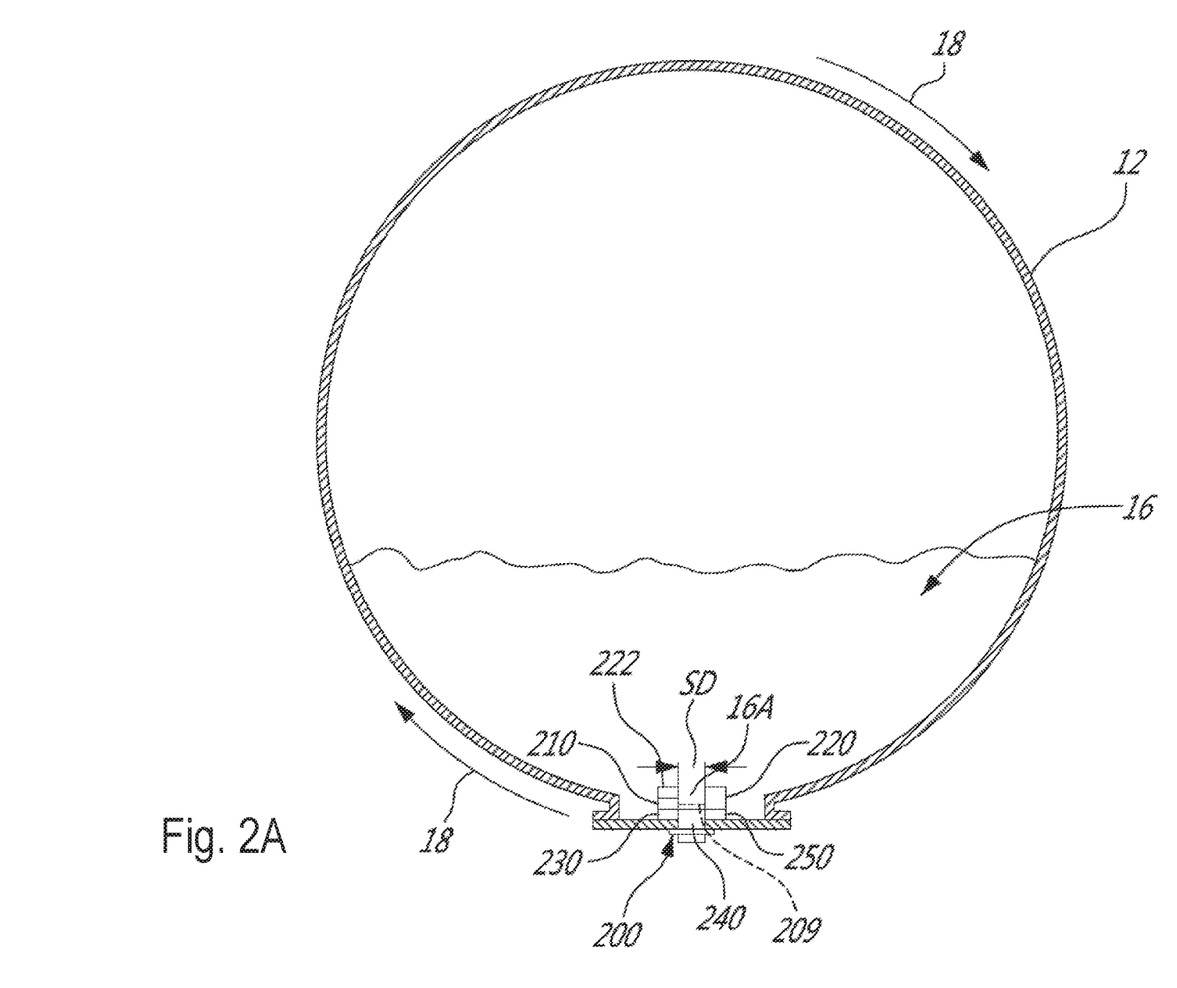
FIG. 2A is a sectional view taken along lines 2-2 of FIG. 1, showing an example of the system of FIG. 1 in an attenuation configuration, in accordance with one or more embodiments.

FIG. 2A shows a section of the drum 12 taken along lines 2-2 of FIG. 1. As illustrated, the drum 12 is loaded with fresh concrete 16 and rotated with respect to arrows 18. An example of the high energy photon probing assembly 200 is shown. The high energy photon probing assembly 200 has a photon path 209, a high-energy photon source 210 configured to emit high energy photons towards the photon path 209, and at least a photon detector, such as first photon detector 220, configured to receive high energy photons from the photon path 209. As can be appreciated, the photon path 209 is immersed in the fresh concrete for a given period of time during the rotation of the drum 12. As shown, the high energy photon source 210 is spaced from the first photon detector 220 by a spacing distance SD. In some embodiments, the spacing distance SD can be about 50 cm, preferably about 75 cm, and most preferably about 100 cm or above. The high energy photon probing assembly 200 is configured and adapted to generate one or more signal(s) indicative of a number of counted events (hereinafter "the number of counted events N") which is representative of the number of high-energy photons that, after having been propagated along the photon path 209 and across a fresh concrete sample 16A handled by the concrete mixer 10, reach the first photon detector 220.

It is noted that the high energy photon source 210 and the photon detector 220 can be enclosed in one or more housings being made of a material transparent to the propagation of such high energy photons. For instance, steel can be envisaged, as well as any other suitable metal. Moreover, in some embodiments, shielding is provided inside the drum 12 to reduce the risks of high energy photon leaving the drum 12.

In some embodiments, the high energy photon probing assembly 200 can have a transmitter 230 for transmitting the number of counted events N through electromagnetic signal(s) (e.g., digital signal(s) and/or analog signal(s)) to the communicating unit 108 shown in FIG. 1. In some embodiments, the transmitter 230 is configured to transmit the number of counted events N directly to the computing device 500 as shown in FIG. 1, without the need of the communicating unit 108.

In some other embodiments, the signal(s) generated by the high energy photon probing assembly 200 can indicate when the high energy photon source 210 emits high energy photons and when high energy photons are received by the first photon detector 220 so that the computing device 500 can determine the number of counted events N by calculating it from the signal(s). In these embodiments, for instance, the first photon detector 220 can include a second photon detector 222 adjacent to the high-energy photon source 210 and opposed to the first photon detector 220 to detect when high energy photons are emitted. The second photon detector 222 can generate a first signal when it receives a high energy photon emitted by the high energy photon source 210, and the first photon detector 220 generates a second signal when it receives the high energy photon emitted by the high energy photon source 210, after propagation along the photon path 209.

The high energy photon source can be an X-ray photon source in some embodiments. Examples of X-ray photon sources can include, but not limited to, rotating anode X-ray tube(s), micro-focus X-ray tube(s), crooked X-ray tube(s), Coolidge X-ray tube, and the like. In some other embodiments, the high energy photon source can be a gamma photon source. Examples of gamma photon source can include, but not limited to, Caesium 137 photon source, Americium-241 photon source, Iodine-131 photon source, Cobalt-60, Iridium-192 and the like. The photons can be collimated and/or focused depending on the embodiment. The high energy photons can be monochromatic or polychromatic. In the latter case, the photon detector can be spectrally resolved so as to provide a number of counted events as a function of frequency or wavelength.

As depicted, the high energy photon probing assembly 200 has a position sensor 240 (e.g., an accelerometer) configured to generate position data indicative of the position of the high energy photon probing assembly 200 relative to the mixer truck 10 over time. For instance, the number of counted events N can be determined when the high energy photon probing assembly 200 is proximate or at its lowest position, i.e., the position shown in FIG. 2A, to ensure that the high energy photon source 210, the first photon detector 220 and the photon path 209 are immersed in the fresh concrete 16 during the measurements.

The high energy photon probing assembly 200 can be powered by a rechargeable power source 250. Any suitable type of rechargeable power source can be provided. For instance, the rechargeable power source can include batteries and can be charged via a power cord, solar panel(s), an induction process, or any other suitable charging means. However, in embodiments where the high energy photon source 210 is a gamma photon source, the high energy photon may not need any powering, thus alleviating the power requirements imparted on the high energy photon probing assembly 200. In such a case, power would be used to power the other components such as the photon detector 220, the computing device 500, communication units, signal/data storage and the like.

Any type of high energy photon probing assembly can be used. For instance, the high energy photon probing assembly 200 shown in FIG. 2A is in an attenuation configuration. In such an embodiment, an attenuation value can be determined by comparing the signals generated by the first and second photon detectors 220 and 230.

Figure 2B:
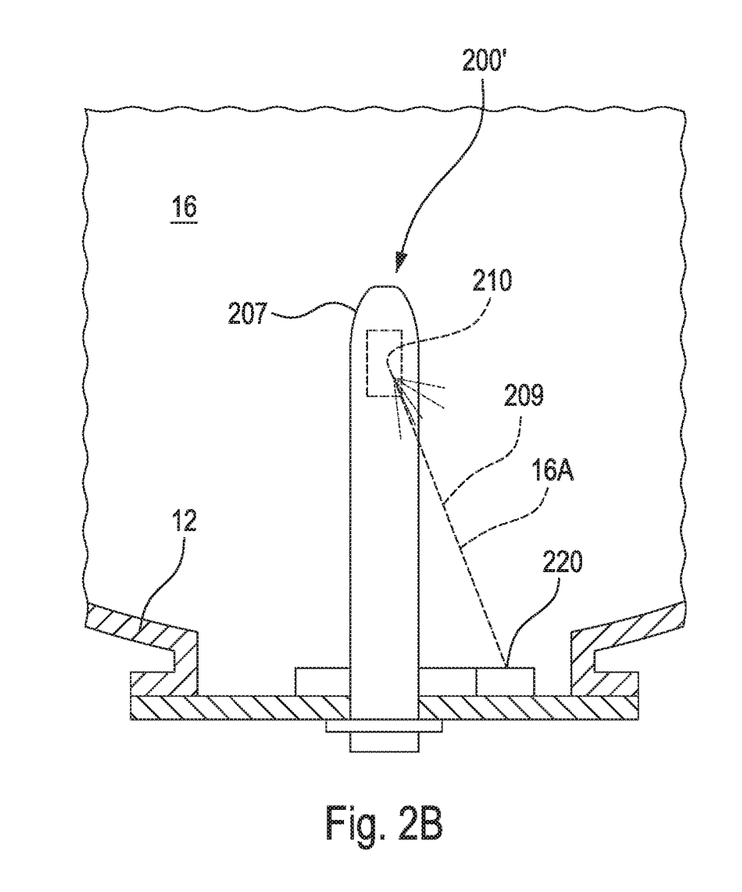
FIG. 2B is a sectional view taken along lines 2-2 of FIG. 1, showing another example of the system of FIG. 1 in an attenuation configuration, in accordance with one or more embodiments.

FIG. 2B shows another example of a high-energy photon probing assembly 200' in an attenuation configuration. In this specific embodiment, the high energy photon source 210 is proximate a tip of a probe 207 mounted inside the drum 12 whereas the photon detector 220 is mounted to an interior wall of the drum 12. The probe 207 can be a rheological probe in some embodiments. However, the probe 207 can be any suitable type of probe. In this case, the fresh concrete sample 16A is the fresh concrete that lies along the photon path 209 which extends substantially linearly between the high energy photon source 210 and the photon detector 220. In such an attenuation configuration, the received photons carry a photon energy similar to a photon energy of the emitted high energy photons as the received and emitted high energy photons share the same wavelength/frequency. In this context, the energy of the photon is to be construed as per $E=hc/\lambda$ where E is photon energy, h is the Planck constant, c is the speed of light in vacuum and $\lambda$ is the photon's wavelength. Accordingly, the generated signal can be indicative of an attenuation between the emitted high energy photons and the received photons. The attenuation can thereby be representative of the number of emitted high energy photons versus the number of received photons. The denser the concrete sample between emission and reception is, the lower the number of high energy photons that actually reach the photon detector 220. An example of such a rheological probe is described in U.S. Pat. No. 9,199,391 B2, the content of which is hereby incorporated by reference.

Figure 2C:
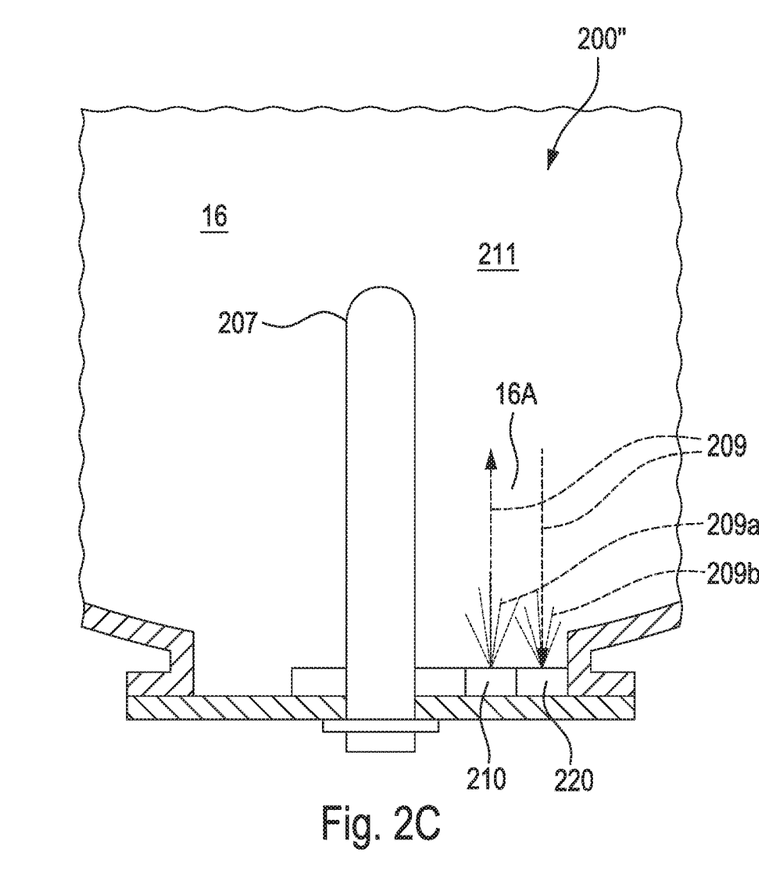
FIG. 2C is a sectional view taken along lines 2-2 of FIG. 1, showing another example of the system of FIG. 1 in a Compton scattering configuration, in accordance with one or more embodiments.

In some other embodiments, such as the one shown in FIG. 2C, the high energy photon probing assembly 200" can be configured into a Compton scattering configuration where the high energy photon source 210 and the photon detector 220 are both oriented towards the fresh concrete sample 16A. In this case, the photon path 209 has a first path portion 209a extending between the high energy photon source 210 and a region 211 immersed in the fresh concrete 16, and a second path portion 209b extending between the region 211 and the photon detector 220. As Compton scattering is the scattering of a high-energy photon by a charged particle, usually an electron. It results in a decrease in energy (increase in wavelength) of the high energy photon (which may be an X-ray or gamma ray photon), called the Compton effect. As high energy photons can be scattered in any direction by any of the molecules present across the photon path 209, only high energy photons which are scattered in the direction of the photon detector 220 may be counted. In this case, the spacing distance is based on the length of the first and second path portions 209a 209b when they are immersed in the fresh concrete 16. In the Compton scattering configuration, the received photons are said to be scattered and carry a photon energy different to a photon energy of the emitted high energy photons. In this case, the generated signal can thus be indicative of Compton scattering occurring along the photon path 209. Other configurations are also.

Figure 3:
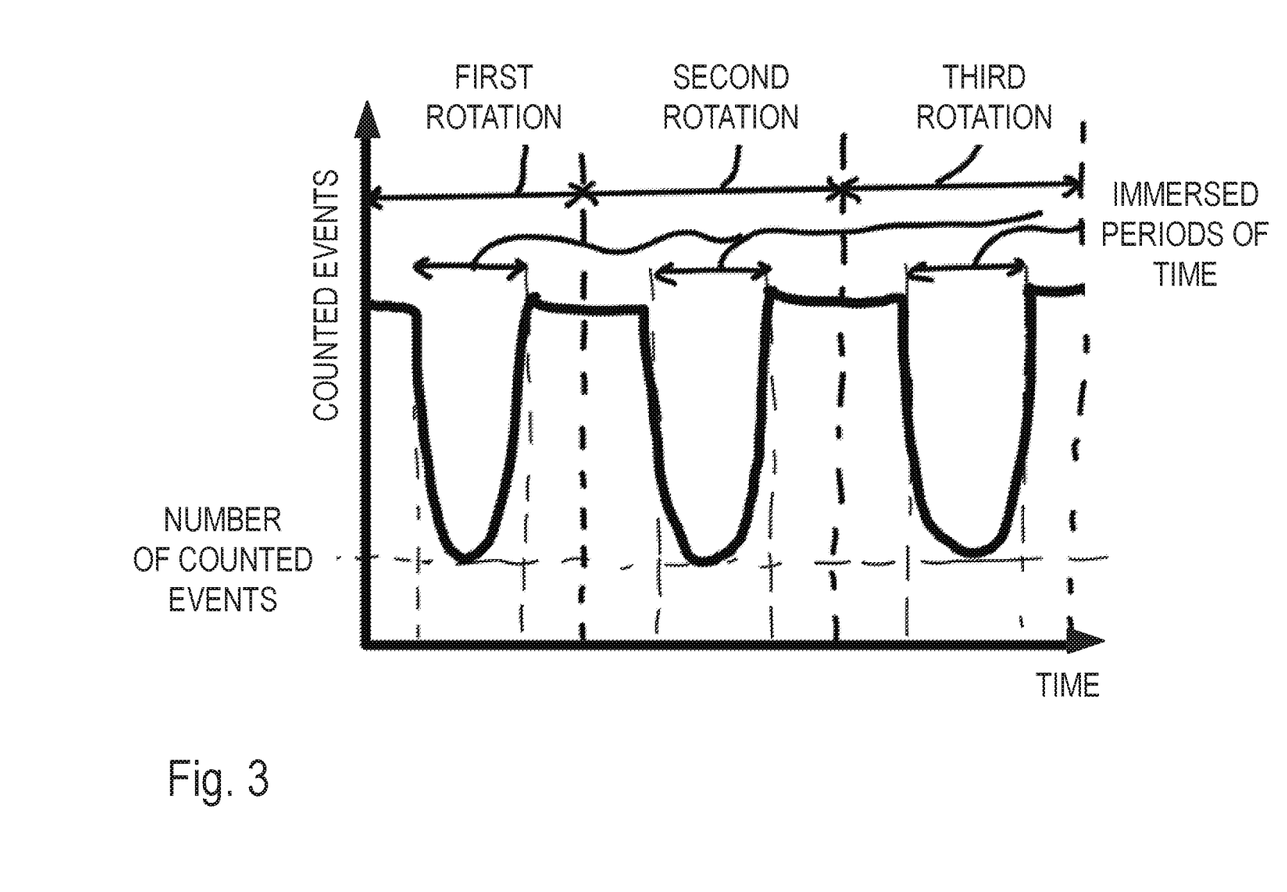
FIG. 3 is a graph showing events counted over time by a photon detector of the system of FIG. 1, in accordance with one or more embodiments.

FIG. 3 shows a graph of counted events versus time as the drum 12 rotates, in accordance with an embodiment. In this example, the drum 12 performs three successive rotations, thereby providing oscillations in the counted events. As shown, the number of counted events can increase when the high energy photon probing assembly 200 is not immersed in the fresh concrete 16 whereas the number of counted events can decrease as the high energy photon probing assembly 200 is immersed in the fresh concrete 16. In some embodiments, the number of counted events that is used in the air content calculations is the number of counted events as measured when the high energy photon probing assembly 200 is partially or wholly immersed in the fresh concrete 16, and preferably when the high energy photon probing assembly 200 lies at or around the bottom of the drum 12. Although the dips of the curve in the three rotations of the drum is constant in this embodiment, as the air content is constant during these rotations, the dips could increase or decrease depending on whether air-entrainment processes are being performed during these rotations.

Figure 4:
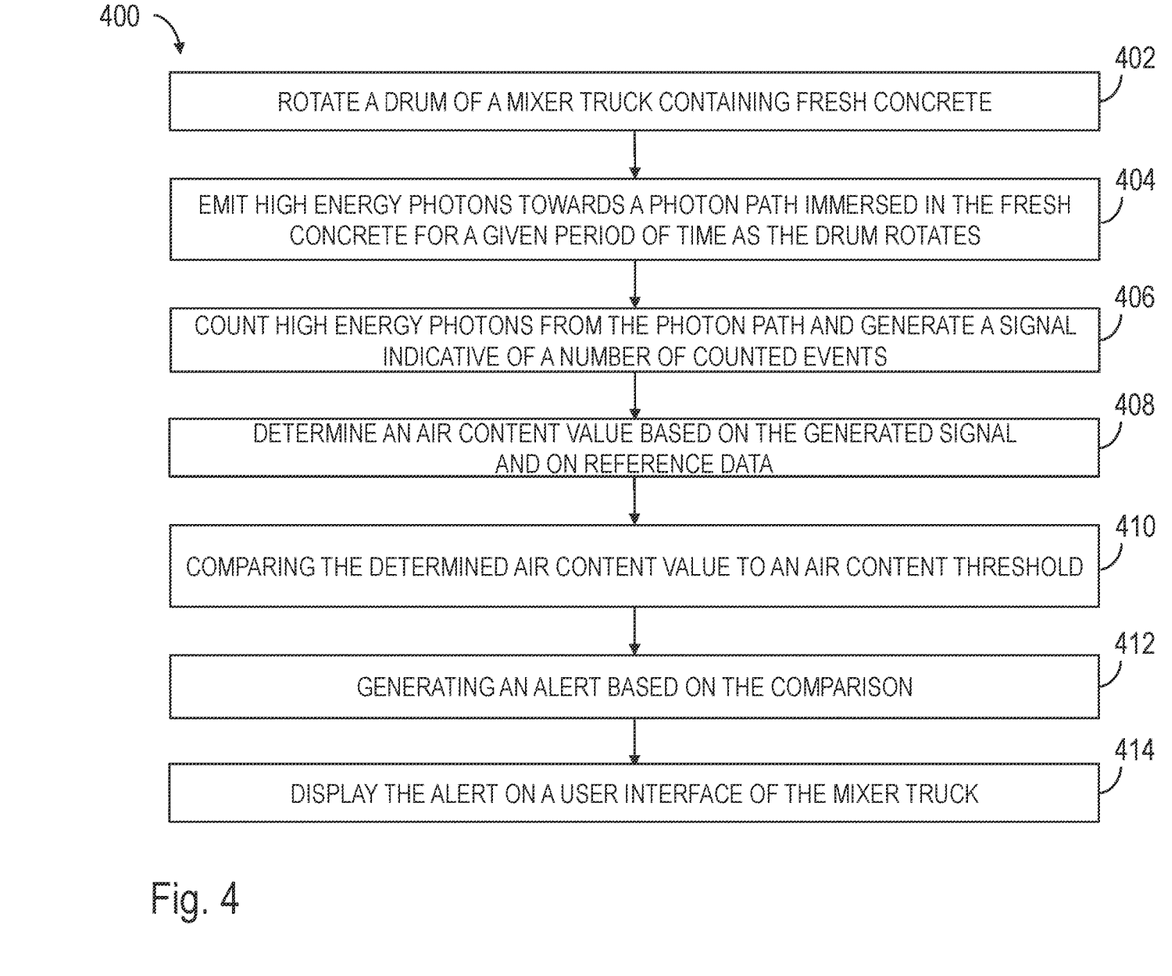
FIG. 4 is a flow chart of an example method for determining an air content value of fresh concrete inside the drum of the concrete mixer truck of FIG. 1, in accordance with one or more embodiments.

FIG. 4 shows a flow chart of a computer-implemented method 400 for determining an air content value AC. As the method 400 can be performed by the computing device 500, reference to FIGS. 1 and 2A will be made in the following paragraphs. In this context, the air content value AC is indicative of the air content of the fresh concrete sample 16A.

At step 402, the drum 12 of the mixer truck 10 is rotated about the rotation axis 14 for at least a given period of time.

At step 404, the high energy photon source 210 emits high energy photons towards the photon path 209 at least when the photon path 209 is immersed in the fresh concrete 16. The emission can occur as the drum 12 rotates or then the drum 12 is immobile, with the photon path 209 being immersed in the fresh concrete 16.

At step 406, the photon detector 220 counts high energy photons received from the photon path 209 at least during a given period of time. The photon detector 220 then generates one or more signal indicative of a number of counted events during the given period of time. The number of counted events N can be determined based on the signal(s) generated by the photon detector 220. As mentioned above, the number of counted events N can either be received directly from the signal(s) or calculated from the signal(s).

At step 408, the air content value AC can be determined based on the generated signal and on reference data. More specifically, in this embodiment, the number of counted events N can be matched to an air content value AC using reference data. The reference data can be obtained previously to the determination of the number of counted events N. The reference data can be obtained from measurements previously made on a fresh concrete sample having the same expected composition, except for different air contents, as the composition of the fresh concrete sample 16A.

The reference data include reference numbers of counted events $N_{ref,i}$ indicative of a number of high-energy photons emitted by the high energy photon source 210 to reach the photon detector 220 via the photon path 209 and across the fresh concrete sample 16A (i being an integer greater than unity). The reference data also include reference air content values $AC_{ref,i}$ indicative of an air content of the fresh concrete sample. Each reference air content value $AC_{ref,i}$ value has reference number of counted events $N_{ref,i}$ associated thereto.

The reference data can be provided in the form of a lookup table or a mathematical relationship associating reference number of counted events to corresponding reference air content values. The reference data is stored in a computer-readable memory accessible by a processor, and can include stored values and stored software instructions.

In the case of the lookup table, for instance, the step 408 can include a step of looking up the reference data to find a given reference number of counted events $N_{ref,i}$ corresponding to the number of counted events N and a subsequent step of determining that the air content value AC corresponds to a reference air content value $AC_{ref,i}$ value associated to the given reference number of counted events $N_{ref,i}$. In this example, the variable i is an integer indicative of the index of the given number of counted events in the lookup table.

In some embodiments, a step of extrapolating the air content value AC using the reference data can be performed. For instance, the step of looking up the reference data can include a step of finding two reference numbers of counted events $N_{ref,j}$, $N_{ref,j+1}$ surrounding the number of counted events N (i.e. $N_{ref,j}<N<N_{ref,j+1}$), and a step of extrapolating the air content value AC based on at least two reference air content values $AC_i$, $AC_j$ associated to the two reference number of counted events $N_{ref,j}$, $N_{ref,j+1}$. In this example, the variable j is an integer indicative of the index of the given number of counted events in the lookup table.

For instance, Table 1 shows reference data T1 associated to a given composition C1 of a fresh concrete sample, and provided in the form of a lookup table. In this case, the composition C1 includes a water cement ("w/c") ratio of 0.5.

It will be noted that this table has been simplified and is provided as a visual support to explain a possible embodiment.

| i | $N_{ref,i}$ [counts] | $AC_{ref,i}$ [%] |
|---|---|---|
| | T1 | |
| 1 | 10000 | 2 |
| 2 | 13000 | 4 |
| 3 | 16000 | 6 |
| 4 | 19000 | 8 |
| 5 | 21000 | 10 |

Table 1 shows reference data T1 for a given composition C1 of a fresh concrete sample In this case, the air content value can be determined based on the lookup table. For instance, the calculation of the air content value can include finding two (or more) reference numbers of counted events surrounding the measured number of counted events N and extrapolating the air content value based on two (or more) reference air content values associated to the two reference numbers of counted events. For instance, for the composition C1, if the number of counted events N is 11500 counts, the air content value can be extrapolated using the couples (10000 counts, 2%) and (13000 counts, 4%), to yield an extrapolated air content value of 3%. In another example, the lookup table can be more exhaustive and the determination of the air content value can be based on a nearest match of a corresponding value of the table, for instance.

Reference data can be provided for more than one composition of fresh concrete. For instance, reference data can be provided for composition of fresh concrete having any acceptable w/c ratio. Reference data can also be provided for composition of fresh concrete including one or more admixtures.

The determination of the air content value can be based on a calculation based on a mathematical relationship in which the air content is a function of the number of counted events. In the case of the mathematical equation, the step 408 can include inputting the number of counted events N into the mathematical equation. For instance, the mathematical relationship can output the air content value AC based on the number of counted events N, i.e., AC=f(N).

In some embodiments, the mathematical relationship can stem from a curve fitting using experimental data. For instance, with a linear curve fitting, the reference data T1 of the given composition C1 can be approximated to the mathematical equation AC=N/1500−4.66. Curve fitting types other than linear can be used depending of the reference data. For instance, fitting can be performed using polynomial functions. A curve fitting algorithm can be used to provide such a mathematical equation based on reference data.

At step 410, the determined air content value AC is compared to an air content threshold $AC_{thres}$. At step 412, the computing device 500 generates an alert based on the comparison. For instance, whether the determined air content value AC is below or exceeds the air content threshold $AC_{thres}$, an alert may be generated. The air content threshold $AC_{thres}$ can be provided in the form of a range. An alert may be generated upon determining that the air content value is below or above the predetermined range. The range can be between 2% and 12%, preferably between 4% and 10%, and most preferably between 4% and 9%. At step 414, the alert is displayed. In some embodiments, the air content value AC can be displayed on the user interface 106 shown in FIG. 1.

In some embodiments, the user interface 106 can include a green LED, a yellow LED and a red LED. In these embodiments, the green LED can be activated as long as the air content value AC is above the air content threshold $AC_{thres}$, the yellow LED can be activated when the air content value AC corresponds to the air content threshold $AC_{thres}$, and the red LED can be activated when the air content value AC is below the air content threshold $AC_{thres}$. Different types of sounds can be substituted and/or added to any of the LED lights. For instance, a sound alarm can be activated when the air content value AC is below the air content threshold $AC_{thres}$.

As it will be understood, the air content threshold $AC_{thres}$ can be associated to a minimal (or maximal) amount of air voids that are required to be present in the fresh concrete to provide sufficient durability against freezing and thawing cycle effects. For instance, if the air content value AC of the fresh concrete sample 16A is below the minimum air content threshold $AC_{thres}$, the durability of the fresh concrete, when hardened, can be below the minimal durability for a given application. The signal can be to avoid pouring the fresh concrete, as its air content may not be acceptable.

As mentioned above, the reference data depend on the composition of the fresh concrete sample. In some embodiments, the method 400 is adapted to be used for only one composition and thus the reference data remain the same throughout the steps of the method 400.

In some embodiments, the reference data used in the method 400 are selected from a plurality of reference data pertaining to a plurality of different compositions of fresh concrete samples in accordance with the composition of the fresh concrete sample in the drum 12 of the mixer truck 10. The composition of such fresh concrete sample can be obtained from an input (e.g., user interface 106 shown in FIG. 1).

For example, reference data ($N_{ref,C1}$, $AC_{ref,C1}$), ($N_{ref,C2}$, $AC_{ref,C2}$) and ($N_{ref,C3}$, $AC_{ref,C3}$) associated to three different compositions C1, C2 and C3, respectively, can be obtained. In this case, if the composition that is received from the input indicates that the composition of the fresh concrete sample is composition C3, then reference data ($N_{ref,C3}$, $AC_{ref,C3}$) are selected from all the other reference data, and then the matching of the number of counted events N to the air content value AC, as per step 408, is based on the selected reference data ($N_{ref,C3}$, $AC_{ref,C3}$).

A computer-implemented method for producing such reference data is also provided. The method has a step of receiving a reference number of counted events counted by a photon detector following a high-energy photon source emitting high energy photons along a photon path leading to the photon detector as the photon path is immersed in a fresh concrete sample for a given period of time. The method has a step of receiving a reference air content value $AC_{ref,1}$ indicative of an air content of the fresh concrete sample. The method has a step of repeating said receiving steps for a plurality of fresh concrete samples of the same composition and of different air contents. The method has a step of producing reference data ($N_{ref}$, $AC_{ref}$) for the composition of fresh concrete by associating the reference numbers of counted events to the corresponding reference air content values. This method of producing reference data can be performed to produce reference associated to another composition of fresh concrete in order to provide, for instance, a plurality of reference data pertaining to a plurality of different compositions of fresh concrete samples.

Figure 5:
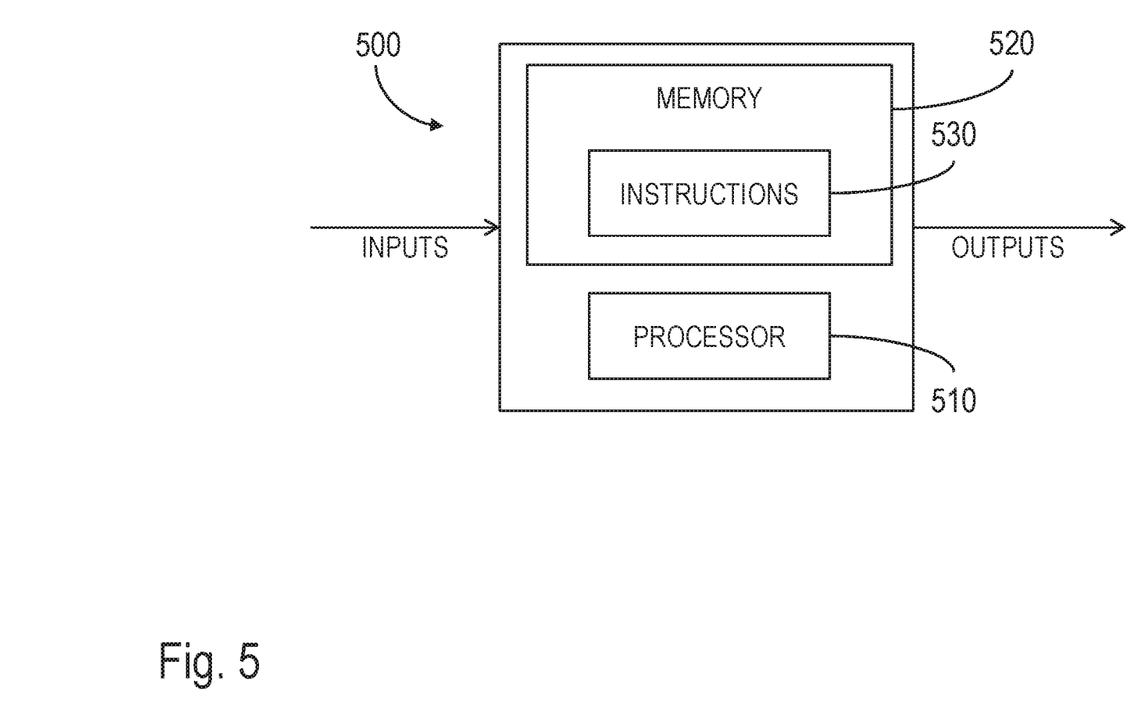
FIG. 5 is block diagram of an example software and hardware implementations of the example method of FIG. 4, in accordance with one or more embodiments.

FIG. 5 shows a schematic representation of an example implementation of the method 400 as a combination of software and hardware components. The computing device 500 is illustrated with one or more processors (referred to as "the processor 510") and one or more computer-readable memories (referred to as "the memory 520") having stored thereon program instructions 530 configured to cause the processor 510 to generate one or more outputs based on one or more inputs. The inputs can comprise one or more signals representative of the number of counted events N and reference data ($N_{ref}$, $AC_{ref}$). The outputs can comprise one or more signals representative of the air content value AC, a signal that the air content value AC is lower or greater than a given air content threshold $AC_{thres}$ or range of threshold values.

The processor 510 can comprise any suitable devices configured to cause a series of steps to be performed so as to implement the computer-implemented method 400 such that instructions 530, when executed by the computing device 500 or other programmable apparatus, can cause functions/acts/steps specified in the methods described herein to be executed. The processor 510 can comprise, for example, any type of general-purpose microprocessor or microcontroller, a digital signal processing (DSP) processor, a central processing unit (CPU), an integrated circuit, a field programmable data array (FPGA), a reconfigurable processor, other suitably programmed or programmable logic circuits, or any combination thereof.

The memory 520 can comprise any suitable known or other machine-readable storage medium. The memory 520 can comprise non-transitory computer readable storage medium such as, for example, but not limited to, an electronic, magnetic, optical, electromagnetic, infrared, or semiconductor system, apparatus, or device, or any suitable combination of the foregoing. The memory 520 can include a suitable combination of any type of computer memory that is located either internally or externally to devices such as, for example, random-access memory (RAM) read-only memory (ROM), compact disc read-only memory (CDROM), electro-optical memory, magneto-optical memory, erasable programmable read-only memory (EPROM), and electrically erasable programmable read-only memory (EEPROM), ferroelectric RAM (FRAM) or the like. Memory 520 can comprise any storage means (e.g., devices) suitable for retrievably storing machine-readable instructions executable by the processor 510.

Figure 6:
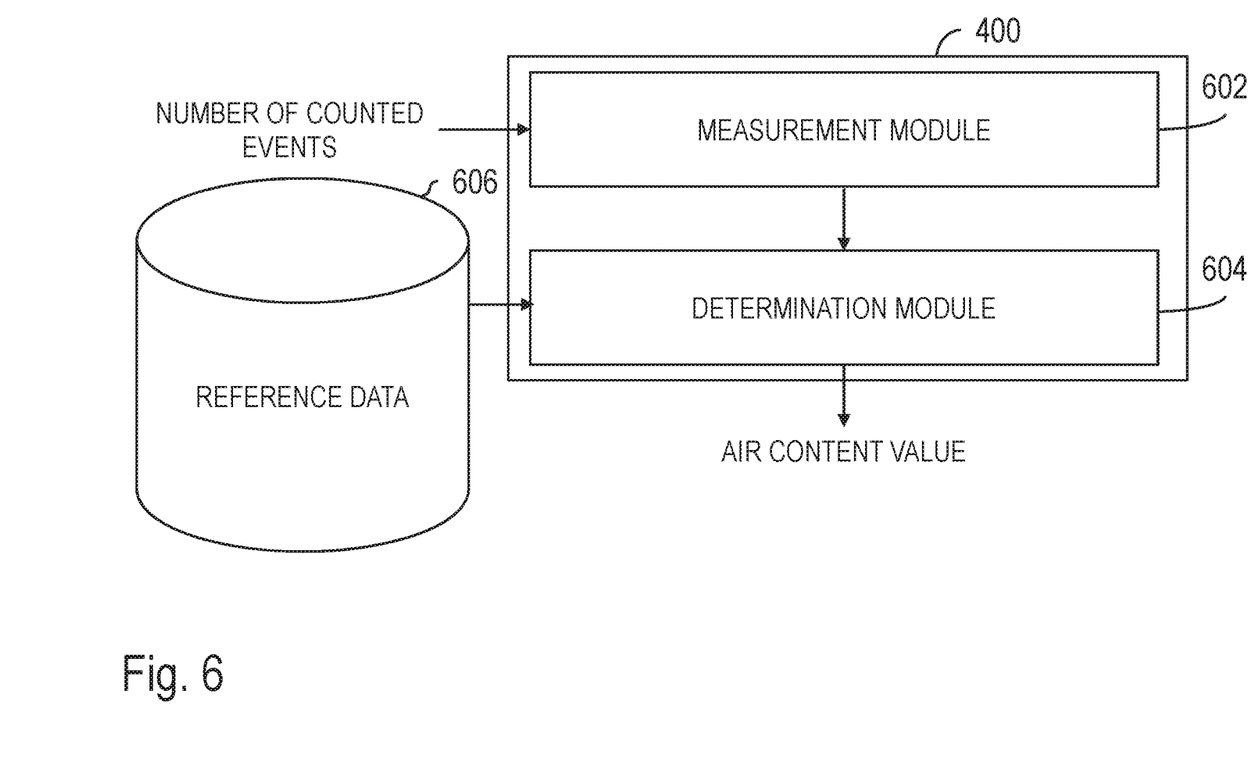
FIG. 6 is a block diagram of an example of a computing device, in accordance with one or more embodiments.

FIG. 6 is a block diagram of an exemplary embodiment of the computing device 500, which can be implemented by the processor 510. As depicted, a determination module 602 and a determination module 604 embody the instructions 530 shown in FIG. 5.

The determination module 602 is configured to receive the signal(s) from the high energy photon probing assembly 200 and to determine the number of counted events N based on the signal(s), as per steps 404 and 406. The determination module 602 can be in communication with the high energy photon probing assembly 200 to receive the signal(s) and, directly or indirectly, the number of counted events N therefrom. The number of counted events N, once determined, is provided to the determination module 604.

The determination module 604 is configured to obtain the reference data and to match the number of counted events N to an air content value AC using the reference data, as per step 408. The determination module 604 can be coupled with a database 606 on which is stored the reference data ($N_{ref}$, $AC_{ref}$, or mathematical relation AC=f(N)) for one or more compositions C1, ..., or $C_N$ of fresh concrete. The database 606 can be provided locally to the computing device 500, or remotely therefrom. In some embodiments, the database 606 corresponds to the memory 520 of the computing device 500.

Once determined, the air content value AC can be displayed on a user interface and/or stored on the database 606. Previously stored air content value can form history data representative of the evolution of the air content over time.

The determination module 604 can also be configured to signal that the air content value is below or above given air content threshold $AC_{thres}$ when the number of counted events N is below or above the number of counted events threshold $AC_{thres}$.

The database 606 can be provided in the form of a single database accessible by the determination module 602 and the determination module 604. Although shown as separate from the computing device 500, the database 606 can be integrated therewith.

Figure 7:
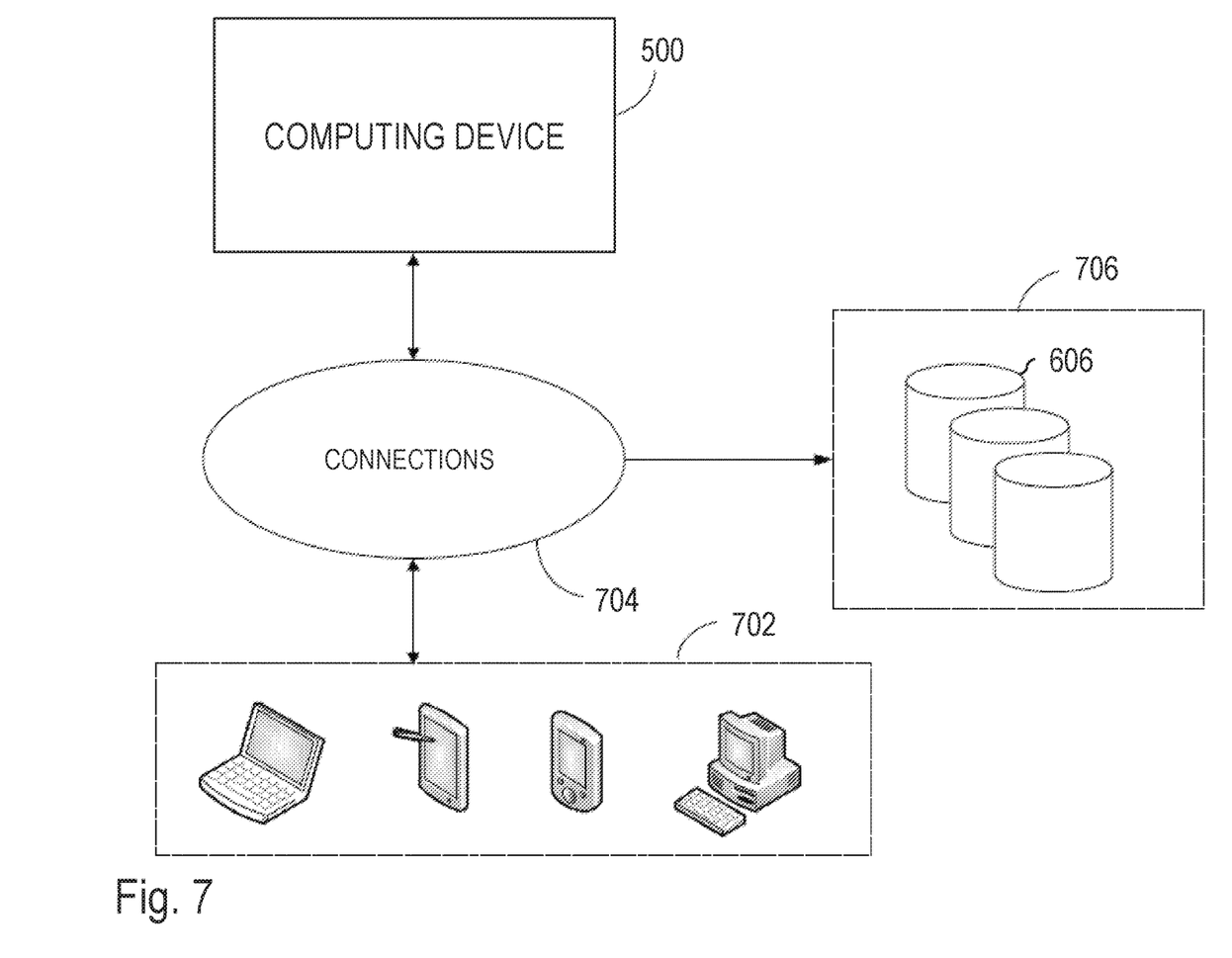
FIG. 7 is a diagram illustrated an example system for determining an air content value, in accordance with one or more embodiments.

Referring now to FIG. 7, in some embodiments, the computing device 500 can be accessible remotely from any one of a plurality of external devices 702 over connections 704. External devices 702 can have an application, or a combination thereof, for accessing the computing device 500. Alternatively, external devices 702 can access the computing device 500 via a web application, accessible through any type of Web browser.

The connections 704 can comprise wire-based technology, such as electrical wires or cables, and/or optical fibers. The connections 704 can also be wireless, such as RF, infrared, Bluetooth, and others. The connections 704 can therefore comprise a network, or others known to those skilled in the art. Communication over the network can occur using any known protocols that enable external devices 702 within a computer network to exchange information. The examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), or SSH (Secure Shell Remote Protocol).

In some embodiments, the computing device 500 is provided at least in part on any one of external devices 702. For example, the computing device 500 can be configured as a first portion provided in the system 100 to obtain and transmit the number of counted events N to a second portion, provided on one of the external devices 702. The second portion can be configured to receive the inputs N, $N_{ref}$ and/or $AC_{ref}$ and perform any one of steps 406, 408, 410, 412 on one of the external devices 702. Alternatively, computing device 500 is provided entirely on any one of the external devices 702 and is configured to receive from a user inputs N, $N_{ref}$ and/or $AC_{ref}$. Also alternatively, the system 100 is configured to transmit, via connections 704, one or more of inputs N, $N_{ref}$ and/or $AC_{ref}$. Other embodiments may also apply.

One or more databases 706, such as database 606 can be provided locally on any one of the computing device 500 and the external devices 702, or can be provided separately therefrom (as illustrated). In the case of a remote access to the databases 706, access can occur via the connections 704 taking the form of any type of network, as indicated above. The various databases 706 described herein can be provided as collections of data or information organized for rapid search and retrieval by a computer. The databases 706 can be structured to facilitate storage, retrieval, modification, and deletion of data on a data storage medium, such as one or more servers. The databases 706 illustratively have stored therein raw data representing a plurality of features of the system 100, the features being, for example, a mathematical relation between the number of counted events N and the air content value AC.

Each computer program described herein can be implemented in a high level procedural or object oriented programming or scripting language, or a combination thereof, to communicate with a computer system. Alternatively, the programs can be implemented in assembly or machine language. The language can be a compiled or interpreted language. Computer-executable instructions can be in many forms, including program modules, executed by one or more computers or other devices. Generally, program modules include routines, programs, objects, components, data structures, etc., that perform particular tasks or implement particular abstract data types. Typically the functionality of the program modules can be combined or distributed as desired in various embodiments.

As can be understood, the examples described above and illustrated are intended to be exemplary only. Various aspects of the present computing device 500 can be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment can be combined in any manner with aspects described in other embodiments. Although particular embodiments have been shown and described, it will be obvious to those skilled in the art that changes and modifications can be made without departing from this invention in its broader aspects. Although the fresh concrete mixer shown in the above-described example is a mixer truck, the fresh concrete mixer can be provided in the form of a stationary mixer in some concrete production plant applications. The scope is indicated by the appended claims.

What is claimed is:

1. A system for determining air content of fresh concrete received in a drum of a concrete mixer, the system comprising:
   a high-energy photon source mounted to the drum, the high energy photon source emitting high energy photons towards a photon path rotating about a rotation axis as the drum rotates, the photon path being immersed in said fresh concrete for a given period of time during said rotating;
   a photon detector mounted to the drum and to which the photon path leads, the photon detector counting high energy photons received from the photon path at least during said period of time; and generating a signal indicative of a number of counted events;
   a computing device communicatively coupled with the photon detector, the computing device determining an air content value of the fresh concrete based on the generated signal and on reference data associating reference numbers of counted events to corresponding reference air content values; comparing said determined air content value to an air content threshold; and generating an alert based on said comparison; and
   a user interface communicatively coupled to the computing device and displaying said alert.

2. The system of claim 1 wherein the high energy photon source is an X-ray photon source or a gamma photon source.

3. The system of claim 1 wherein the photon path extends linearly between the high energy photon source and the photon detector.

4. The system of claim 3 wherein the received photons carry a photon energy similar to a photon energy of the emitted high energy photons, the generated signal being indicative of an attenuation between the emitted high energy photons and the received photons.

5. The system of claim 1 wherein the photon path has a first path portion extending between the high energy photon source and a region immersed in said fresh concrete, and a second path portion extending between the region and the photon detector.

6. The system of claim 5 wherein the received photons carry a photon energy different to a photon energy of the emitted high energy photons, the generated signal being indicative of Compton scattering occurring along the photon path.

7. The system of claim 1 further comprising at least an accelerometer for generating position data indicative of the position of the photon path relatively to the concrete mixer.

8. The system of claim 1 wherein both the high energy photon source and the photon detector are mounted on an interior wall of the drum of the concrete mixer.

9. The system of claim 1 wherein the photon detector is a first photon detector proximate to the high-energy photon source, the system further comprising a second photon detector distal to the high-energy photon source.

10. A computer-implemented method for determining air content of fresh concrete received in a drum of a concrete mixer, the method comprising:
    receiving a signal indicative of a number of events counted by a photon detector following a high-energy photon source emitting high energy photons along a photon path leading to the photon detector during rotation of the drum;
    determining the number of events counted during a given period of time while the photon path is immersed in the fresh concrete received in the drum;
    matching the determined number of events to an air content value of the fresh concrete based on reference data associating reference numbers of counted events to corresponding reference air content values;
    comparing said air content value to an air content threshold;
    generating an alert based on said comparison; and
    displaying said alert.

11. The computer-implemented method of claim 10 wherein the reference data include a lookup table associating the reference numbers of counted events to the corresponding reference air content values.

12. The computer-implemented method of claim 11 wherein said matching includes:
    looking up the reference data to find a given reference number of counted events corresponding to the number of counted events; and
    determining that the air content value corresponds to a reference air content value associated to the reference number of counted events.

13. The computer-implemented method of claim 12 wherein said looking up includes finding at least two reference numbers of counted events surrounding the number of counted events and extrapolating the air content value based on at least two reference air content values associated to the at least two reference numbers of counted events.

14. The computer-implemented method of claim 10 wherein the reference data include a mathematical relation associating reference numbers of counted events to the corresponding reference air content values.

15. The computer-implemented method of claim 14 wherein said matching includes:
  inputting the number of counted events into the mathematical relation; and
  determining that the air content value corresponds to a result of said inputting.

16. The computer-implemented method of claim 10 wherein said reference data are associated to a composition of said fresh concrete sample.

17. The computer-implemented method of claim 16 wherein, prior to said matching, the method further comprises:
  selecting the reference data associated to a composition of the fresh concrete sample among a plurality of reference data pertaining to a plurality of fresh concrete samples of different compositions;
  wherein said matching uses the selected reference data.

18. The computer-implemented method of claim 17 wherein the composition is obtained from an input.

19. A computing device for determining air content of fresh concrete received in a drum of a concrete mixer, the computing device comprising:
  a memory having stored thereon program code executable by a processor; and
  at least a processor configured for executing the program code, the memory and the at least a processor being configured for performing the steps of the computer-implemented method of claim 10.

20. The computing device of claim 19 wherein the reference data associate reference numbers of counted events and corresponding reference air content values for a plurality of fresh concrete samples of different compositions.

21. The computing device of claim 19 wherein the reference data include at least one of a lookup table and a mathematical relation associating reference numbers of counted events with corresponding reference air content values.

22. A computer-implemented method for producing reference data, the computer-implemented method comprising:
  receiving a reference number of counted events counted by a photon detector following a high-energy photon source emitting high energy photons along a photon path leading to the photon detector as the photon path is immersed in a fresh concrete sample for a given period of time;
  receiving a reference air content value indicative of an air content of the fresh concrete sample;
  repeating said receiving steps for a plurality of fresh concrete samples of the same composition and of different air contents; and
  producing reference data for the composition of fresh concrete by associating the reference numbers of counted events to the corresponding reference air content values.

23. The computer-implemented method of claim 22 further comprising performing said receiving, repeating and producing steps for at least another composition of fresh concrete.

24. A concrete mixer truck comprising:
  a frame;
  a drum rotatably mounted to the frame, the drum receiving fresh concrete and having a rotation axis at least partially horizontally oriented relative to the vertical;
  a high energy photon source mounted to the drum, the high energy photon source emitting high energy photons towards a photon path rotating about the rotation axis as the drum rotates, the photon path being immersed in said fresh concrete for a given period of time during rotation of the drum;
  a photon detector mounted to the drum and to which the photon path leads, the photon detector counting high energy photons received from the photon path at least during said period of time; and generating a signal indicative of a number of counted events;
  a computing device communicatively coupled with the photon detector, the computing device determining an air content value of the fresh concrete based on the generated signal and on reference data associating reference numbers of counted events to corresponding reference air content values; comparing said determined air content value to an air content threshold; and generating an alert based on said comparison; and
  a user interface communicatively coupled to the computing device and displaying said alert.

25. The concrete mixer truck of claim 24 wherein the high energy photon source is an X-ray photon source or a gamma photon source.

26. The concrete mixer truck of claim 24 wherein the photon path extends linearly between the high energy photon source and the photon detector.

27. The concrete mixer truck of claim 26 wherein the received photons carry a photon energy similar to a photon energy of the emitted high energy photons, the generated signal being indicative of an attenuation between the emitted high energy photons and the received photons.

28. The concrete mixer truck of claim 24 wherein the photon path has a first path portion extending between the high energy photon source and a region immersed in said fresh concrete, and a second path portion extending between the region and the photon detector.

29. The concrete mixer truck of claim 28 wherein the received photons carry a photon energy different to a photon energy of the emitted high energy photons, the generated signal being indicative of Compton scattering occurring along the photon path.

30. The concrete mixer truck of claim 24 further comprising at least an accelerometer for generating position data indicative of the position of the photon path relatively to the concrete mixer.

31. The concrete mixer truck of claim 24 wherein both the high energy photon source and the photon detector are mounted on an interior wall of the drum of the concrete mixer.

* * * * *